United States Patent [19]
Plowman

[11] 3,964,112
[45] June 22, 1976

[54] DENTAL CUSPIDOR WITH FLUID RECIRCULATION SYSTEM

[75] Inventor: Richard E. Plowman, York, Pa.

[73] Assignee: Dentsply Research & Development Corporation, Milford, Del.

[22] Filed: May 27, 1975

[21] Appl. No.: 581,059

[52] U.S. Cl. .................................... 4/262; 4/263; 4/266; 32/1
[51] Int. Cl.² ................................... A61C 17/04
[58] Field of Search ............ 4/262, 261, 263, 264, 4/265, 266, 10, 90, 115; 32/1, 64

[56] References Cited
UNITED STATES PATENTS

| | | |
|---|---|---|
| 3,067,433 | 12/1962 | Dietz et al. ........................ 4/115 |
| 3,226,733 | 1/1966 | Ashton ............................... 4/263 |
| 3,440,669 | 4/1969 | Boester .............................. 4/10 |
| 3,613,131 | 10/1971 | Stram et al. ....................... 4/263 |
| 3,653,078 | 4/1972 | Buchtel et al. .................... 4/263 |
| 3,842,448 | 10/1974 | Kahn ................................. 4/263 |

Primary Examiner—Henry K. Artis

[57] ABSTRACT

A water recirculation system is described wherein the discharge of one or more dental cuspidors is rendered reuseable and continuously used in the operation of a water sealed vacuum pump in a dental vacuum discharge system.

6 Claims, 1 Drawing Figure

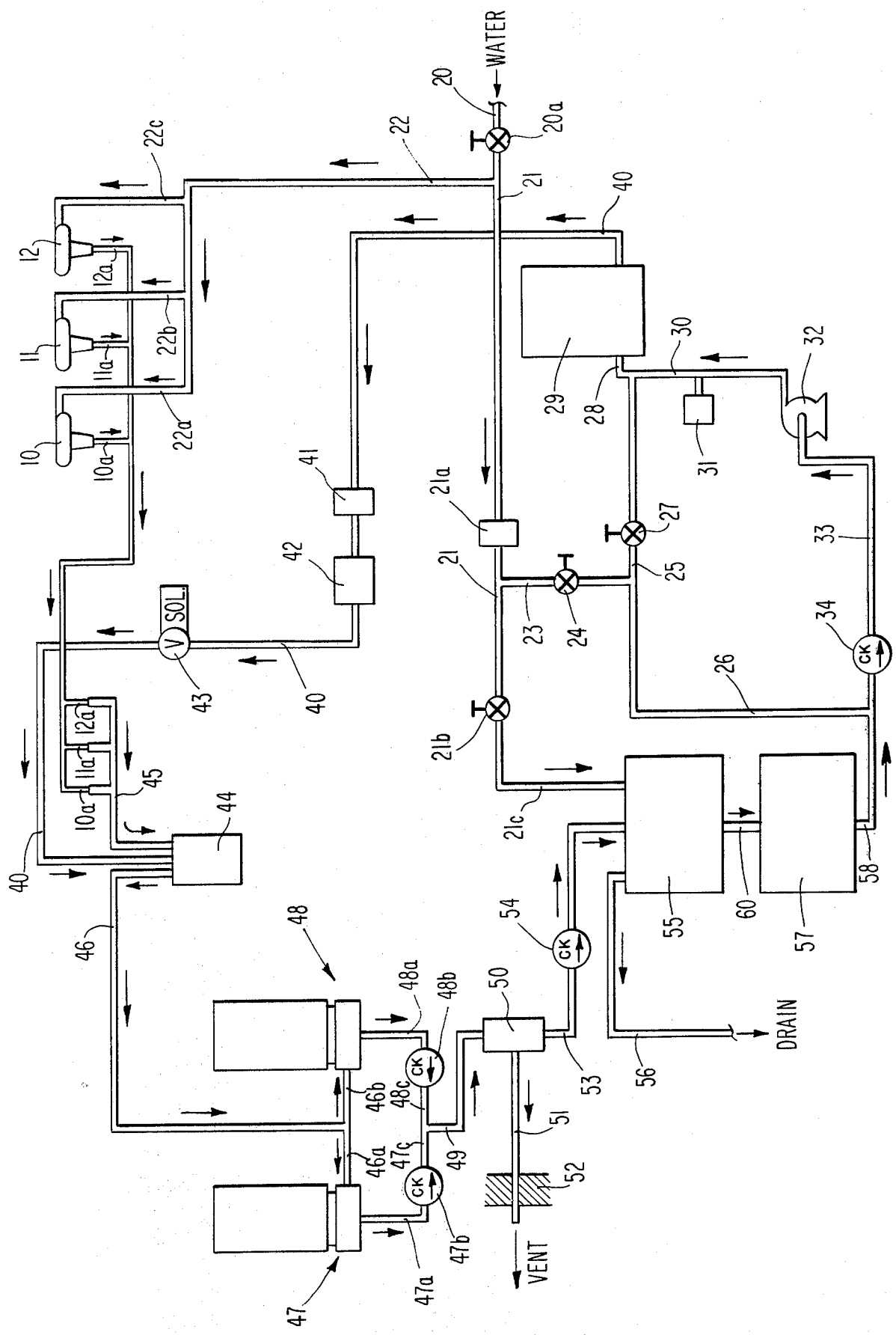

DENTAL CUSPIDOR WITH FLUID RECIRCULATION SYSTEM

BACKGROUND

The present invention relates to a vacuum discharge fluid recirculation system for dental cuspidors.

The present system comprises an improvement upon prior developments, such as that disclosed in U.S. Pat. No. 3,842,448 to Kahn et al.

It is well known that the operation of a dentist's office can involve the use of great quantities of water. If only fresh water is used, the dentist can, therefore, experience very large costs for water supply.

The demand for water in a dentist's office primarily is a result of the use of dental cuspidors, both fixed and hand held. In these familiar devices, flushing water is introduced under pressure and is designed to carry away the substances, both fluid and particulate, discharged by the patient.

As indicated in the Kahn Patent, it has previously been realized that savings can be achieved if the discharge water from cuspidors is recycled. In the Kahn Patent, it is contemplated that the discharged fluid shall be directed back into the cuspidor, after filtration to remove the particulate matter and offensive odor. Such a system creates the need for a relatively high degree of treatment, not only in terms of particle removal, but also for purposes of deodorization. It is usually also necessary to render the discharge fluid colorless prior to reintroducing the same into the cuspidor.

The present system is a departure from the above described techniques. In the present system, only fresh water is used for the purpose of flushing the cuspidor. The cuspidors, which preferably are of the demand type, i.e., which are operable so as to require fresh water only when demanded by the patient and/or the dentist, discharge into a suction evacuation system.

The evacuation system includes a vacuum pump which creates suction to assist in the discharge from the cuspidor. In the present system the discharged water is filtered but, in contrast to prior systems, is not passed back into the cuspidor. Instead, the discharged water is utilized to keep the vacuum pump primed. Accordingly, it is not necessary, with the present system to reach the same high level of particulate filtration, odor removal and de-colorization as is required in prior systems in which the discharge fluid is recirculated back into the cuspidors themselves. The elimination of the aforesaid requirements makes it possible to utilize a simpler, less costly system without substantially increasing the amount of fresh water used.

The above advantages and others will be appreciated from the following detailed description and claims and from the drawing.

THE DRAWING

The drawing is a schematic diagram of the preferred embodiment of the present invention.

DESCRIPTION OF THE PREFERRED EMBODIMENT

The present invention is depicted in connection with a series of hand-held dental cuspidors such as the cuspidors 10, 11 and 12. (There may be more such cuspidors and the system is equally adaptable to fixed cuspidors.)

The cuspidors 10–12, which may be in different rooms, are equipped with switches (not shown) whereby the person using them can turn on the source of water. Fresh water from a supply line 20 enters a fresh water line 22 which, in turn, feeds the individual fresh water conduits 22a, 22b and 22c of the cuspidors 10, 11 and 12, respectively.

Each cuspidor is equipped with a drain, 10a, 11a and 12a, respectively. In turn, the drains are connected to a vacuum discharge line or manifold, 45. The manifold 45 discharges into a solids separator 44. Manifold 45 is maintained under a vacuum through line 46, which vacuum is created in line 46 by a pair of water pumps 47 and 48. Such pumps may be of the MVS type sold by Dentsply International Inc. Under normal conditions, the pumps are turned on at the beginning of each day by a main switch (not shown) in the dental office, and operate continuously throughout the working day. A large volume of water is needed, accordingly, since the pumps require water to maintain suction.

The solids separator 44 may be of any well-known type and is designed to permit the separation of solid or particulate matter, such as dental filling particles, etc., from the fluid. This is usually accomplished by permitting the mass of fluid and particles to remain in the tank, such as the tank 44, for a time sufficient to allow the heavier-than-water particles to sink to the bottom of the receptical.

As indicated, after the particles and other solids have been removed in tank 44, the fluid is removed therefrom under suction through vacuum line 46. Line 46 communicates with the pumps 47 and 48 through lines 46a and 46b, respectively. Pump 47 discharges the fluid through a conduit 47a through a check valve 47b and into a conduit 47c which communicates with a drain 49. Similarly, pump 48 pumps the fluid through a conduit 48a, a check valve 48b and into a conduit 48c which discharges into drain 49 also.

The fluid then passes into the air and water separator 50. The air-water separator may be of the type sold by Dentsply International Inc. in connection with its MVS type vacuum systems. The separator 50 is effective to separate air and gases which are discharged into the atmosphere through a tube 51 which passes through a wall 52.

The remaining liquids drain through line 53, through a check valve 54 under gravity and into a particle filter bed 55. The bed 55 is equipped with an overflow and backflush drain 56. The particle bed 55 drains through conduit 60 into a second filter bed 57. The filters 55 and 57 are preferably of the activated charcoal type and are sufficient to remove impurities in the fluid. (Actually, where desired, the use of filters may be eliminated in the present system line the water is not passed back into the cuspidors.) The water then passes through a drain 58 at the bottom of filter 57 through a check valve 34, into a conduit 33. A pump 32 pumps the water through a line 30 into a pressure tank 29 in which there is an air head. The system is equipped with a pump pressure switch 31 which controls pressure in tank 29 and in the lines to the vacuum pumps. From the pressure tank, the water moves through conduit 40, through a strainer 41, a pressure regulator 42 and discharges through lne 40 into the solids separator 44. Alternatively, line 40 may be connected directly to the input lines 46a, 46b of pumps 47 and 48, bypassing separator 44.

The passage of the recirculated fluid from tank 29 through line 40 is controlled by solenoid valve 43 which opens when pumps 47 and 48 are operated.

It will be observed that fresh water is available to maintain a desired equilibrium in the recirculation system through pipe 21 when valve 21b is opened.

Additionally, fresh water from the supply 20 can be used for backflushing and cleaning the filters by opening valve 20a and valve 24. In addition, circulation water from the pressure tank 29 can be used for backflushing by opening the valve 27.

In the foregoing fashion, the vacuum pumps 47 and 48 may be kept running with wastewater fluid recycled through the system. Accordingly, it is not necessary to constantly introduce fresh water into the system to keep the pumps 47 and 48 primed.

From the foregoing, it will be understood that the present system advantageously provides means whereby fresh water only is used in dental cuspidors, thereby providing the optimum aesthetic effect and sanitary conditions for the dentist and his patients. Moreover, this is accomplished in a system wherein the cuspidors or like devices are provided with vacuum evacuation discharge means, which is highly preferred. In contrast to prior systems, the present apparatus does not require a constant supply of fresh water for the pumps of the vacuum system, but utilizes recirculated fluid for that purpose.

The foregoing description illustrates preferred embodiments of my invention. However, the concepts employed may, based upon such description, be employed in other embodiments without departing from the scope of the invention. Accordingly, the following claims are intended to protect the invention broadly, as well as in the specific forms shown therein.

I claim:

1. A fluid system comprising:
    a. a cuspidor;
    b. a fresh water supply for the cuspidor;
    c. vacuum means for removing wastewater from said cuspidor;
    d. a vacuum pump for said vacuum means;
    e. means for rendering said wastewater reuseable;
    f. means for passing said wastewater into the vacuum pump while bypassing said cuspidors whereby said vacuum pump is continuously maintained in a primed condition during operation.

2. The invention of claim 1 wherein the cuspidor is a dental cuspidor.

3. A fluid system for dental use comprising:
    a. a cuspidor;
    b. means for supplying fresh water into said cuspidor;
    c. a drain for removing wastewater from said cuspidor;
    d. suction means connected to said cuspidor drain for assisting in the evacuation of wastewater from said cuspidor;
    e. a vacuum pump for said suction means, said vacuum pump having an inlet and an outlet for wastewater;
    f. means for returning at least a portion of the wastewater initially discharged through the outlet of the vacuum pump to the inlet of said pump without first passing through the cuspidor.

4. The invention of claim 3 wherein the return means includes an air and water separator.

5. The invention of claim 3 wherein the return means includes a particle filter means.

6. The invention of claim 3 wherein the return means includes a water pump and pressure tank.

* * * * *